United States Patent [19]
Helfenbein et al.

[11] Patent Number: 5,511,554
[45] Date of Patent: Apr. 30, 1996

[54] REAL-TIME ARTIFACT REMOVAL FROM WAVEFORMS USING A DYNAMIC FILTER HAVING A FIXED DELAY

[75] Inventors: Eric D. Helfenbein, Sunnyvale; Richard D. Pering, Palo Alto; James M. Lindauer, San Francisco; Don Goodnature, Santa Clara, all of Calif.

[73] Assignee: Hewlett Packard Company, Palo Alto, Calif.

[21] Appl. No.: 281,046

[22] Filed: Jul. 27, 1994

Related U.S. Application Data

[63] Continuation-in-part of Ser. No. 134,780, Oct. 12, 1993.
[51] Int. Cl.⁶ .......................... A61B 5/0205; A61B 5/0456
[52] U.S. Cl. ........................... 128/706; 128/670; 128/700
[58] Field of Search ........................... 128/630, 668, 128/670–672, 680, 687, 695, 696, 700, 706, 708

[56] References Cited

U.S. PATENT DOCUMENTS 5,392,780  2/1995  Ogino et al. ............................ 128/670

Primary Examiner—William E. Kamm
Assistant Examiner—George Evanisko

[57] ABSTRACT

During sampling, a finite impulse response (FIR) filter separates a composite signal into two components, non-cardiac physiological phenomena and cardiac artifacts. The length of the filter window dynamically varies to produce an output signal in which the cardiac frequency and any associated harmonics are suppressed with a fixed delay. The FIR filter is applied to the patient signal and lags the patient signal by at least one interval between triggering events. When the present interval between triggering events passes by the filter window, the window length is gradually adjusted to have the same length as the next period such that the window length is centered between two adjacent triggering events. The difference between the present interval and the next interval is evenly distributed or subtracted across the filter window between centerings.

19 Claims, 9 Drawing Sheets

REAL-TIME ARTIFACT REMOVAL FROM WAVEFORMS USING A DYNAMIC FILTER HAVING A FIXED DELAY

This is a continuation-in-part of a patent application having a Ser. No. of 08/134,780, filed on 12 Oct. 1993, by Pering, et al.

FIELD OF THE INVENTION

The invention pertains generally to patient monitors and more particularly to an apparatus and method for isolating physiological phenomena in real-time by removing cardiac artifacts that occur at a varying cardiac frequency and harmonics of that frequency.

BACKGROUND OF THE INVENTION

Transducers are commonly used in patient monitoring to gather information about a patient's condition. The resulting signals are often a mixture of physiological phenomena. In general, this is an inherent property in all electrical and pressure signals derived from mechanical movement in the body, in particular, organ movement such as that by the diaphragm and the heart. Unfortunately, the intrinsic characteristics of these measured signals are often overwhelmed by the strength of the artifacts introduced by the heart. Of the organs, the heart usually has the most pronounced and most rapid motion, which can be picked up very easily by the transducers when measuring another phenomenon. In other words, the electrical signals from the heart, often "drown out" the signals of interest. For example, respiratory impedance is a mixture of electrical changes due to respiration and electrical changes due to mechanical cardiac events. Observing each phenomena in isolation is desirable for medical analysis and patient monitoring.

One technique to isolate the phenomena is fixed-frequency filtering. This method has limited success since the frequency ranges overlap for heart and respiration rates. As a result, removing the cardiac artifacts at fixed frequencies often fails altogether or significantly distorts the filtered respiration signal. Since the physiological artifacts, such as those due to cardiac or other muscle activity, vary in time with response to stress and illness, fixed-frequency filtering is ineffective at artifact removal.

In "Canceling the Cardioenic Artifact in Impedance Pneumoraphy", IEEE/Seventh, Annual Conference of the Engineering in Medicine and Biology Society, pp 855–859, Sahakian et al attempted adaptive filtering by applying a cardiac artifact template which was then subtracted from the respiratory impedance (RI) waveform. The timing signal for adapting the signal averaged cardiac artifact template was the output of a conventional QRS detector. The QRS detections further provided the pacing for subtracting the cardiac artifact template from the RI waveform. This technique failed to take into account the beat-to-beat variations in the amplitude and shape of the cardiac artifact: the shape of the current cardiac artifact is often significantly different from that of the signal-averaged cardiac artifact, so that simply subtracting the averaged cardiac artifact is often ineffective and may even introduce new artifacts. Furthermore, template-adaptive filtering is not responsive enough to remove beat-to-beat variations.

In the "Elimination of Breathing Artifacts from Impedance Cardiograms at Rest and During Exercise", Medical and Biological Engineering & Computing, January 1988, pp 13–16, Eiken and Segerhammer experimentally reduced breathing artifacts contained in an impedance cardiogram by using a moving-window technique in conjunction with linear regression analysis. The window length had a width that was jump adapted at the start of each new cardiac cycle to be equal to the length of the previous cardiac cycle. Using the sample points within this window, they then performed a linear regression to find a straight line segment that was the "best" straight line approximation to the data within the window. Finally, the center point of the regression line was used to estimate the value of the respiration signal with the cardiac artifact, removed. The window length was updated and a linear regression analysis was performed when the center sample passed the R-beat. This technique was inadequate for two reasons: linear regression is computationally expensive and jump adaptation introduces artifacts into the resulting filter output.

SUMMARY OF THE INVENTION

In real time, a finite impulse response (FIR) rectangular filter separates a composite patient signal into two components: non-cardiac physiological phenomena and cardiac artifacts as the signal is being sampled. The length of the filter window is dynamically varied to produce a smooth output signal in which effects of a varying cardiac frequency and any associated harmonics are suppressed. The varying cardiac frequency is determined by marking the cardiac events in a reference cardiac signal. The filter window length is initially set to be the interval between the first two cardiac events, and is aligned between these two events. The filter window is then advanced across the data, and is gradually adjusted to have the same length as the next cardiac interval when the filter is aligned between the next pair of cardiac events. The delay from the most recent input sample to the midpoint of the filter window is kept constant, while the filter length expands and contracts symmetrically around this midpoint. The difference between the present and next cardiac intervals is evenly distributed across the filter window between centerings. Thus, there is a time-average analysis for each time the midpoint of the filter window is advanced by a sample such that the output of the filter has as fixed delay from the filter input.

DETAILED DESCRIPTION OF THE PREFERRED EMBODIMENTS

Figure 1:
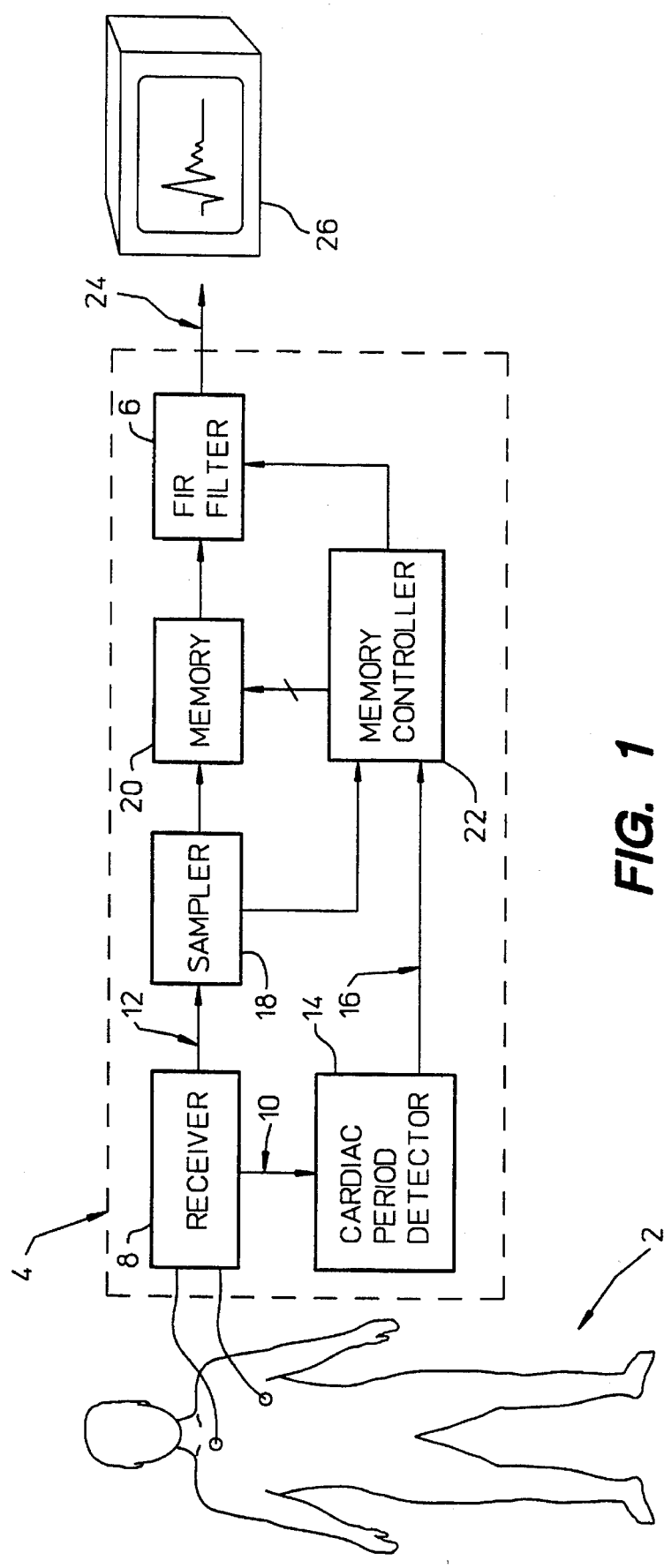
FIG. 1 is a block diagram that shows the main electrical components of the invention, which is shown attached to a patient.

FIG. 1 shows a patient 2 attached to a patient monitor 4 that has a dynamically varying filter 6, preferably one that has a finite impulse response (FIR). At least two physiological signals from the patient 2 are measured, for example, as voltages by a receiver 8: a reference cardiac signal 10 and a composite signal 12 that contains physiological phenomena such as respiratory impedance or central venous pressure. Signals from all of the patient's physiological phenomena are assumed to be contaminated by the reference cardiac signal 10.

Initially, a cardiac period detector 14 detects cardiac events contained within the reference cardiac signal 10 and determines a cardiac frequency, which can vary between the cardiac events, and produces a cardiac interval 16. At the same time, the sampler 18 digitally samples the composite signal 12, which is then stored in memory 20. A memory controller 22 uses the cardiac interval 16 to adjust, the length of the finite impulse response (FIR) filter 6, which may be a rectangular filter, and applies the FIR filter to the sampled data stored in memory. The FIR filter 6 produces a filtered composite signal 24 in which the non-cardiac phenomenon corresponds to the dominant component.

The filtered composite signal 24 that represents the non-cardiac phenomena can be displayed on a conventional monitor 26 or further analyzed by a computer (not shown) to detect periodic events in the non-cardiac signal; this is explained in greater detail below. If the non-cardiac events are not within a predetermined tolerance region, an indicator of an abnormal patient condition is activated. Furthermore, the out-of-tolerance non-cardiac signal may be displayed on the monitor 26.

Figure 2:
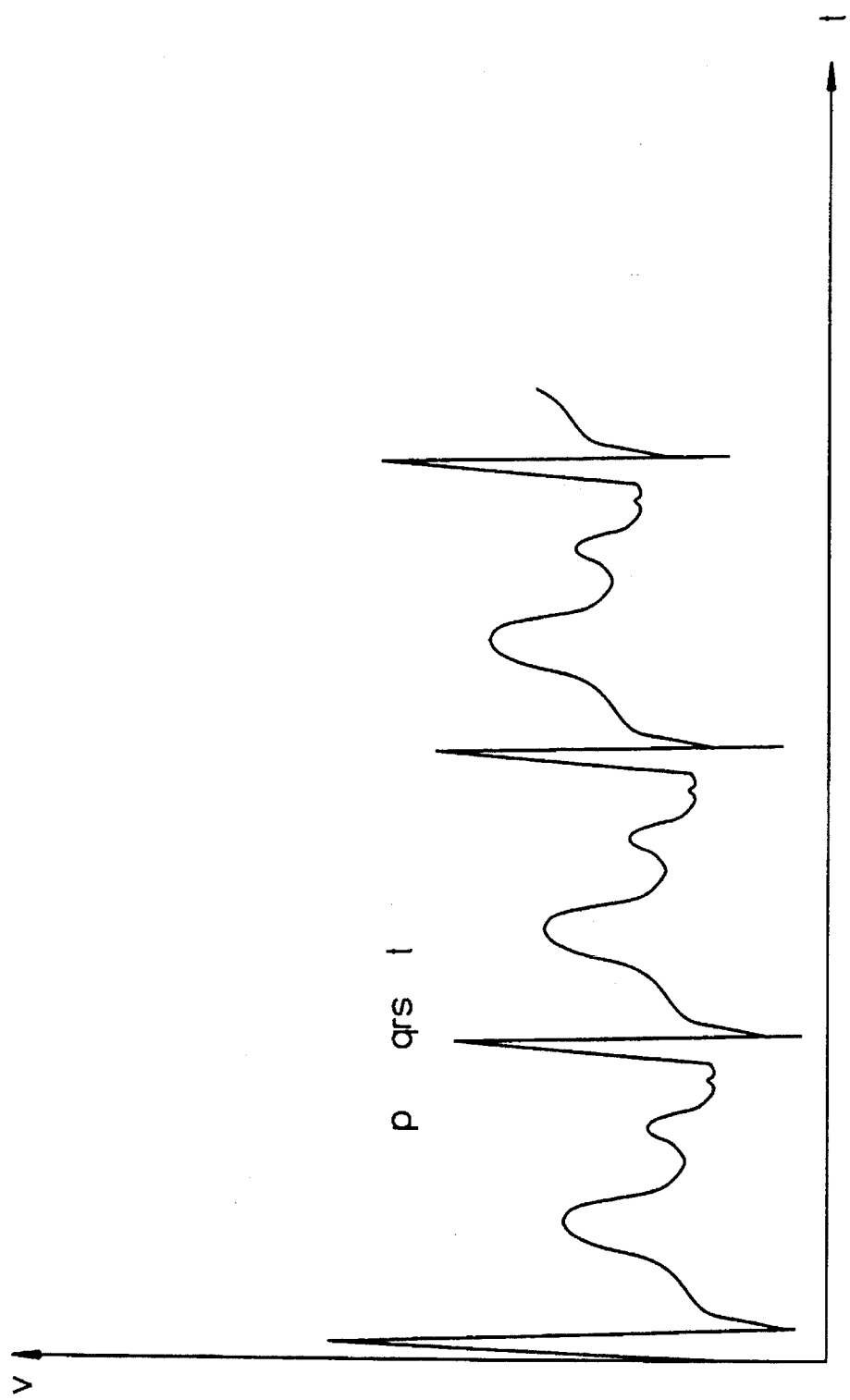
FIG. 2 illustrates an electrical representation of a cardiac event.

FIG. 2 is an electrical representation of a series of cardiac events. Since the cardiac frequency varies with physical activity, stress, and condition of the patient, the events are preferably detected from some relatively constant feature of the reference cardiac signal 10, such as peak voltage. The cardiac event is a composite of well-known "PQRST" waves. The P wave corresponds to the depolarization of the atria; the length of the P wave indicates the time necessary to depolarize the atria. The QRS wave reflects the spread of depolarization through the ventricles. The amplitude of the QRS wave is much greater than that of the P wave because the ventricles have more tissue mass than the atria. During the QRS wave, the atria repolarize. The ventricles remain depolarized during the ST wave. The T wave is generated as the ventricles repolarize.

Figure 3:
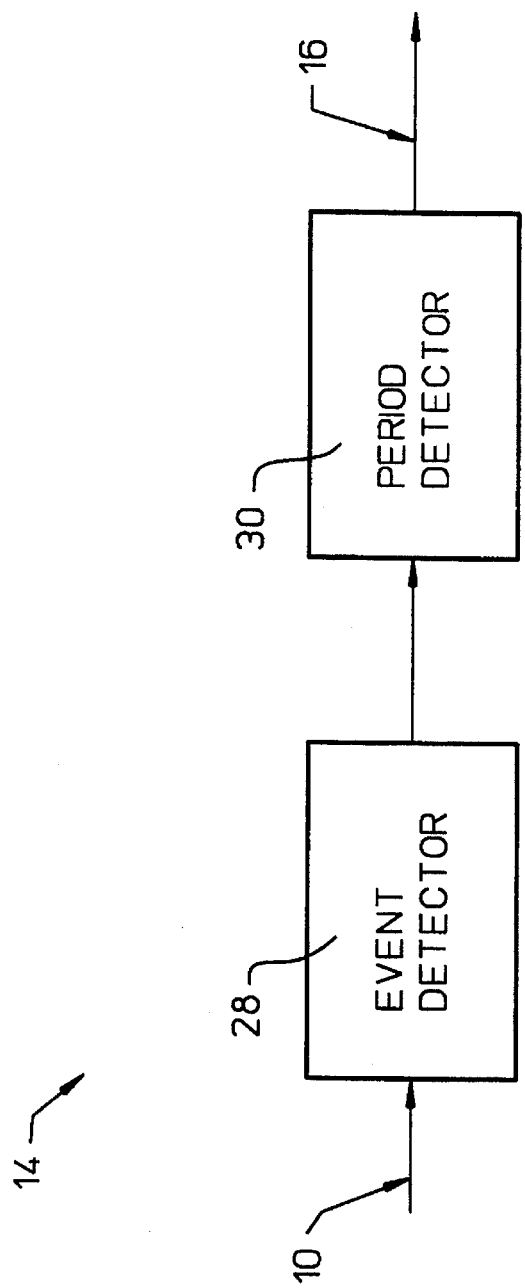
FIG. 3 is a functional block diagram of a cardiac period detector in FIG. 1.

FIG. 3 is a functional block diagram of the cardiac period detector 14 shown in FIG. 1. The cardiac period detector 14 is composed of a cardiac event detector 28 and a cardiac interval detector 30. The event detector 28 receives the reference cardiac signal 10 and searches for the reference points in the reference cardiac signal 10. The cardiac interval detector 30 is connected to the cardiac event detector 28. The interval detector 30 counts the number of samples between adjacent cardiac events and produces the cardiac interval 16. The cardiac interval 16 is defined as the number of samples that are taken between adjacent cardiac events, preferably at a constant sampling rate. The cardiac interval 16 is updated at each event detection to indicate the variable cardiac period. Any portion of the "PQRST" waves can be used as reference point and thus defines a cardiac event.

The cardiac period detector 14 can be constructed by any technique known to those in the art, such as those suggested by Freisen et al. in "A Comparison of the Noise Sensitivity of Nine QRS Detection Algorithms", IEEE Transactions Biomedical Engineering, p.85–98 (1990).

Figure 4:
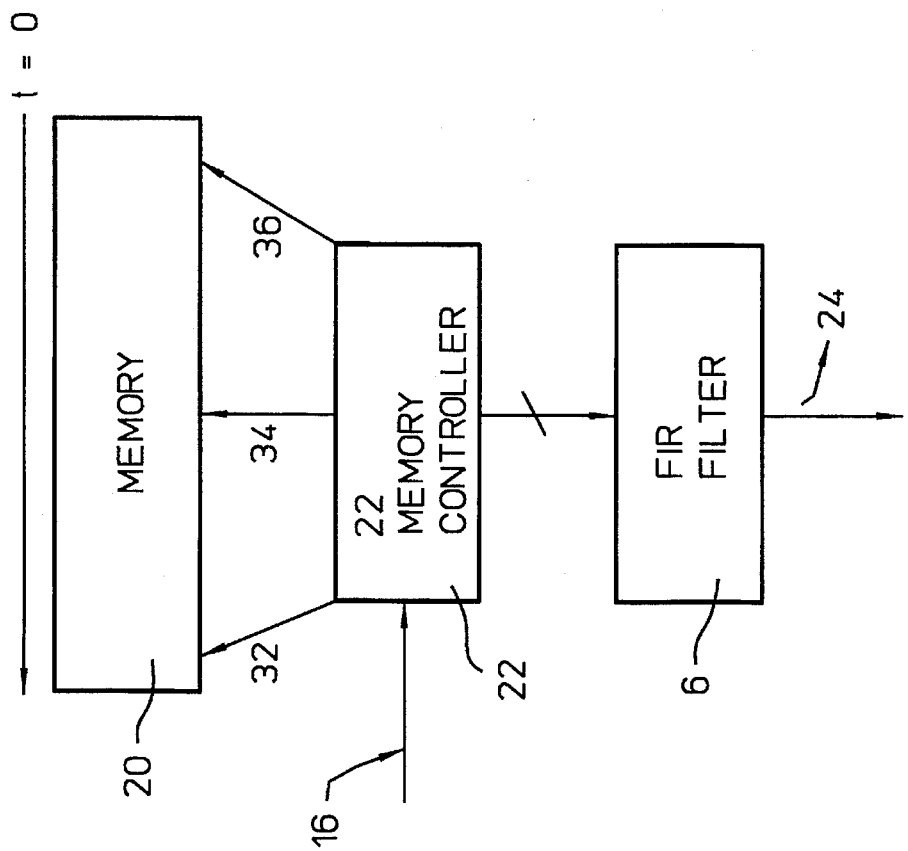
FIG. 4 is a functional block diagram of an arrangement for controlling filter length $F_L$ of the FIR filter shown in FIG. 1.

FIG. 4 is a functional block diagram of an arrangement for controlling the filter length $F_L$ of the FIR filler shown in FIG.

1. The memory controller 22 accesses the memory 20 using a left pointer 32, midpointer 34, and a right pointer 36, which in combination define a filler length $F_L$ and set the delay of the FIR filter 6; this is explained in greater detail below. The filter 6 has a filter length $F_L$ that is dynamically adjusted to match the cardiac interval when the filter window is centered between two adjacent cardiac events. A rectangular filter provides the optimal reduction of the cardiac frequency and its harmonics. The rectangular filter, as is well-known, is a type of symmetrical moving-average filter with equal weights.

The filter length $F_L$ is gradually adjusted to correspond to a complete cardiac interval. As the midpoint of the window advances sample by sample, the filter length $F_L$ is smoothly adapted around the midpoint toward the next cardiac interval to avoid sudden jumps in the filter output. Without the gradual adjustment of the filter length $F_L$, the resulting time-averaged signal would introduce distortion.

According to the invention, the filter length $F_L$ is set equal to the present cardiac interval. The cardiac interval is chosen as the filter length $F_L$ because the cardiac frequency and any associated harmonics will then be cancelled or "notched out" of the non-cardiac signal during averaging using any symmetric filter. Thus, the FIR filter is designed to have the "zeros" of the transfer function at the harmonics of the cardiac frequency. The zeros appear as periodic "holes" in the impulse response when viewed in the frequency domain. An additional constraint (the well-known Nyquist criterion) is that the sampling rate must be selected to be at least twice the highest frequency of the phenomena of interest in the composite signal to avoid aliasing.

The properties of a finite impulse response (FIR) filter are well known in the art and are described in many standard texts on digital signal processing or time series analysis. A FIR filter can be described roughly as a type of signal averaging and weighting device that moves or "sweeps" over a series of values. The general structure of an FIR filter can be represented as follows:

$$y(t) = \sum_{m=0}^{n-1} w(m) \cdot x(t-m) \qquad \text{Eqn. 1}$$

where y(t) is the output value of the filter at time t;

x(t−m) is the input value to the filter m time units before time t; and w(m) is the m'th of a set of n weighting factors. In other words, the output y(t) from the FIR filter at any given time t is formed as a weighted sum of the most recent input value x(t) and the n−1 previous input values x(t−1), x(t−2) . . . x[t−(n−1)]. Weighting is done by multiplying each input value x(t−m) m time units ago by the corresponding m'th weight value w(m). If the weights w(m) are different, then some of the input values are allowed to contribute more to the output, value than others. If all the non-zero weights are the same over an interval w(j), . . . w(n−1), 0≦j≦n−1, then the FIR filter is said to be rectangular, and is referred to as a moving average filter. The set of non-zero, equal weights w(j), . . . w(n−1) are called the filter "window".

For a symmetric filler (e.g. the rectangular filter), the output of the filter relative to the input corresponds to the location of the midpoint of the filter weights over the input signal. Thus, the filter "delay" is equal to the distance between the most recent input sample and the midpoint of the filter window. When this distance remains constant, the filter has a fixed delay; when this distance varies, the filter has a time-varying delay. Therefore, adapting the filter length $F_L$ by changing the left and right halves of the window around a window midpoint which remains at a fixed distance from the most recent input sample has a fixed delay. Alternatively, adapting the filter length $F_L$ by keeping one end of the filter window fixed relative to the most recent input sample and updating in one direction only will have a time-varying delay.

A filter having a fixed delay has several advantages. The differences in time between events (e.g. breaths) occurring in the input signal and the corresponding difference in time between the same events in the filter output will remain constant. Thus, event-to-event intervals (e.g. breath-to-breath) can be accurately measured. Another advantage is that the reference cardiac signal 10 can be easily subtracted from the composite signal 12 to produce the filtered composite signal 24 which contains non-cardiac phenomena. To do this, the composite signal 12 is shifted by the constant filter delay before subtracting the corresponding points. This would be difficult for a time varying delay, especially when the delay is a non-integer number of sample intervals.

Alternatively, other known symmetric FIR filters, such as the Hamming, Hanning, and Blackman, may be used, but at the cost of efficiency. In this embodiment, the preferred rectangular filter has been implemented in software.

Figure 5:
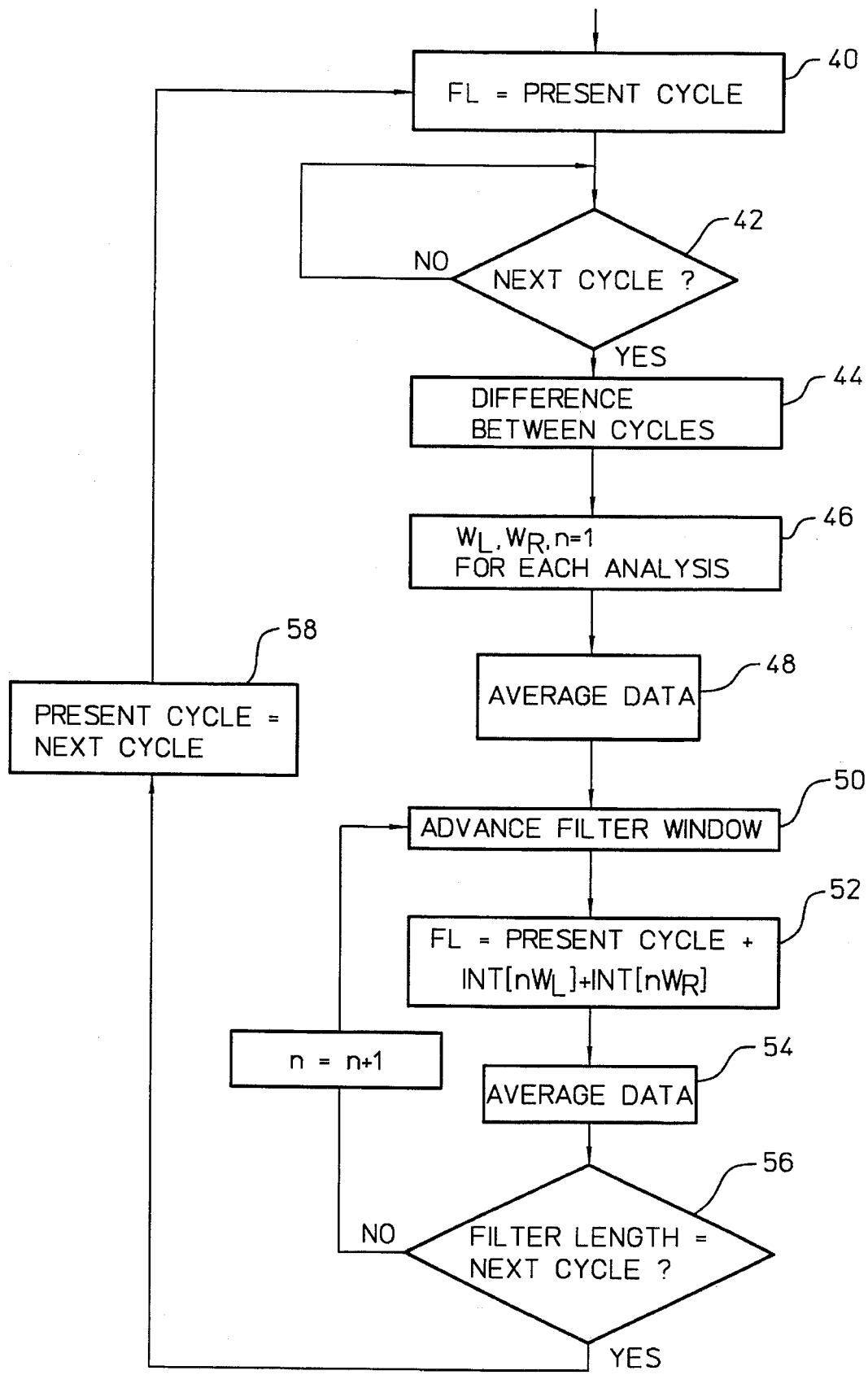
FIG. 5 shows the process diagram for distributing a next cardiac interval as a filter window moves across a series of cardiac data values.

FIG. 5 shows a flowchart, of the process for distributing the next cardiac interval as the filter window traverses from the present cardiac interval to the next cardiac interval. The FIR filter length $F_L$ is chosen to be the present interval. The next cardiac interval is determined from the series of cardiac events. The difference between the present cardiac interval and the next cardiac interval is determined. This difference is then distributed over the number of samples between the midpoints of the present and next cardiac intervals to determine a left and right window correction factors $W_L$, $W_R$. The length of the filter determines the number of samples to be averaged. During each analysis period, the left, pointer, midpointer, and right pointer are each advanced by one sample except during window changes. Window changes occur when either edge can be updated by an integral multiple of the corresponding edge correction factor: $INT[nW_L]$, $INT[nW_R]$. The INT[] function represents conversion from a fractional number to an integer, and may employ either truncation or rounding to the nearest integer. The filter length $F_L$ is updated until the filter length $F_L$ equals the next cardiac interval. At this point, the next cardiac interval becomes the present cardiac interval and the distribution process is repeated.

Figure 6:
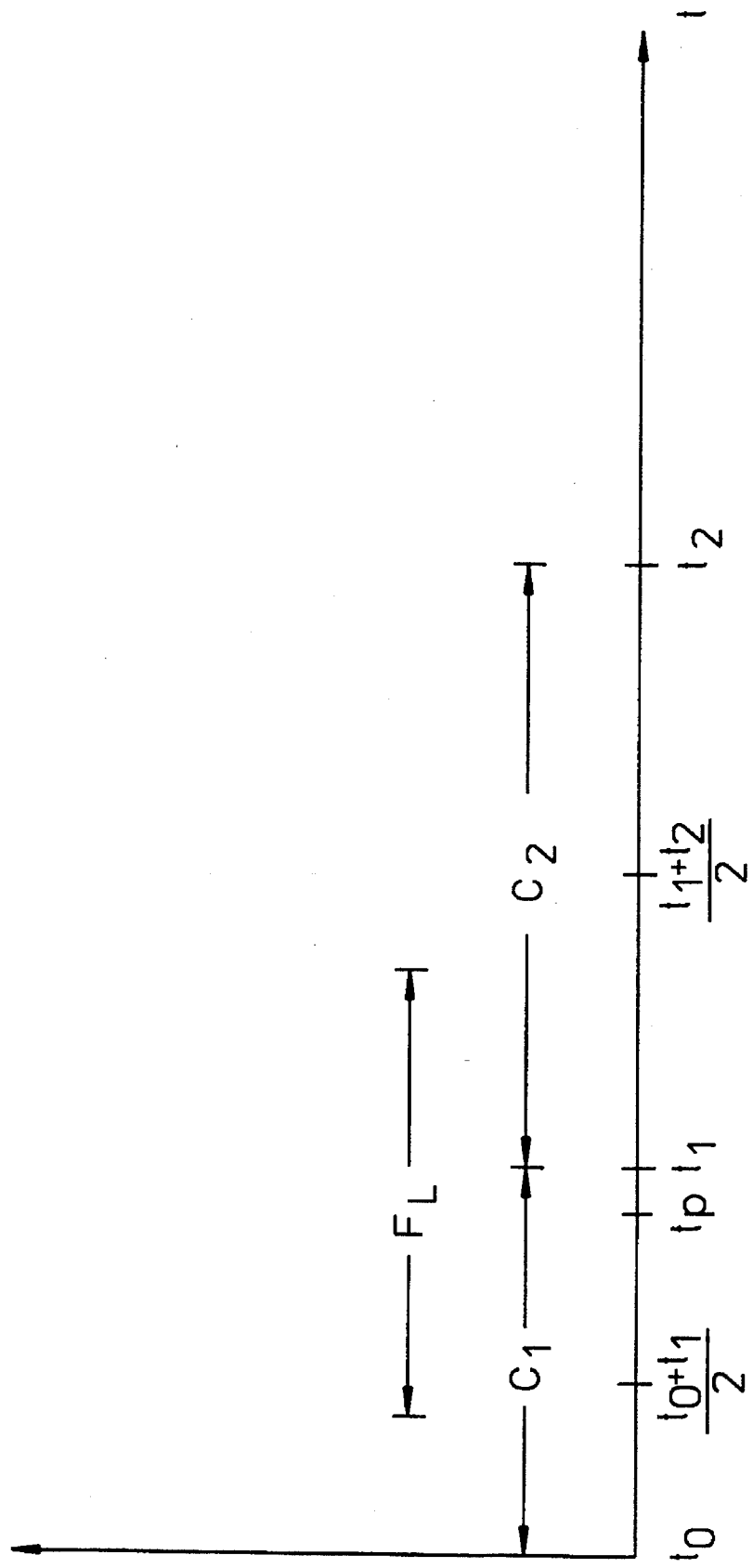
FIG. 6 illustrates a general application of dynamically adapting the filter length $F_L$ of the FIR filter.

FIG. 6 illustrates a general application of dynamically adapting the filter length $F_L$ of FIR filter. Cardiac events occur at times $t_0$, $t_1$, and $t_2$. $C_1$ and $C_2$ are adjacent cardiac intervals. In this example $C_2$ has a longer duration than $C_1$. $t_p$ corresponds to the present position of the filter midpointer. Initially, $t_p$ is at the midpoint of $C_1$ and the filter length $F_L$ is equal to $C_1$. Equation 2 describes the current filter window length as the filter midpointer $t_p$ advances from the midpoint of the present cardiac interval $C_1$ to the midpoint of the next cardiac interval, at which the filter length will be equal to $C_2$. The left and right edge correction factors, $W_L$ and $W_R$ are given by:

$$F_L = C_1 + \frac{(C_2 - C_1)}{\left(\frac{C_2}{2} + \frac{C_1}{2}\right)} \left(t_p - \frac{(t_0 + t_1)}{2}\right) = \quad \text{Eqn. 2}$$

-continued
$$C_1 + \frac{2(C_2 - C_1)}{(C_2 + C_1)} \left(t_p - \frac{(t_0 + t_1)}{2}\right)$$

$$W_L = W_R = \frac{C_2 - C_1}{C_2 + C_1}$$

The correction factors give the length each edge of the filter window must be adjusted at each step n from one cardiac interval to the next.

The above equations specify the filter window length and edge correction factors in units of "time", e.g. seconds. In a digital implementation, these factors must be converted to "number of samples" by multiplying $nW_L$, $nW_R$, and $F_L$ by the sampling frequency S given in hertz (i.e. samples per second). Since samples are integral, the results of these calculations are truncated or rounded to the nearest integral number. The filter length (in samples) may have to be slightly non-symmetric about the filter midpointer if the current filter length contains an even number of samples. The effect of this temporary non-symmetry will be minimized if the sampling rate is sufficiently high.

This method dynamically varies the filter length $F_L$ produce a smooth output signal in which cardiac phenomena are suppressed. After the present interval between cardiac events passes by the filter window, the filter length $F_L$ coincides with the cardiac interval when the window is centered between two adjacent cardiac events. This adjusts the position of the "zeros" of the filter to be at the cardiac frequency and its harmonics, thus notching out any cardiac artifact at those frequencies. The difference between the present interval and the next interval is evenly distributed when the endpoints of the filter length $F_L$ are between reference points. The evenness in distribution depends both on the sampling frequency and the difference between the cardiac intervals. Higher sampling frequencies allow smoother adaptation.

The filter length $F_L$ is adjusted by the memory controller 22, which is connected to the memory 20 and the cardiac period detector 14. The controller 22 has the left pointer 32, midpointer 34, and right pointer 36, which define which samples (in particular, how many) in memory 20 are to be averaged. The memory controller 22 advances the midpointer 34 by one composite sample for every sampling period and gradually adjusts the left and right pointers 32, 36 such that the length of the adaptive window is the cardiac interval 16 when the midpointer 34 is centered between two adjacent reference points. The memory controller 22 takes the difference between the next cardiac interval and compares it to the current cardiac interval. This difference will be evenly distributed over the distance between the midpoints of the present and next cardiac intervals by the memory controller 22 in whole samples.

For example, if the length of the present cardiac interval is 10 samples and the length of the next cardiac interval is 14 samples, the filter length $F_L$ must be lengthened by 4 samples over a distance of 12 samples. During each averaging, the left pointer 32, midpointer 34, and right pointer 36 are each advanced by one sample except during filter length $F_L$ changes. The filter length $F_L$ can be changed by not advancing the left pointer 32, advancing the midpointer 34 by one sample, and advancing the right pointer 36 by two samples every sixth averaging across the data. Thus, the filter length $F_L$ increases every sixth averaging. Alternatively, the filter length can be changed at the third and ninth steps.

Figure 7:
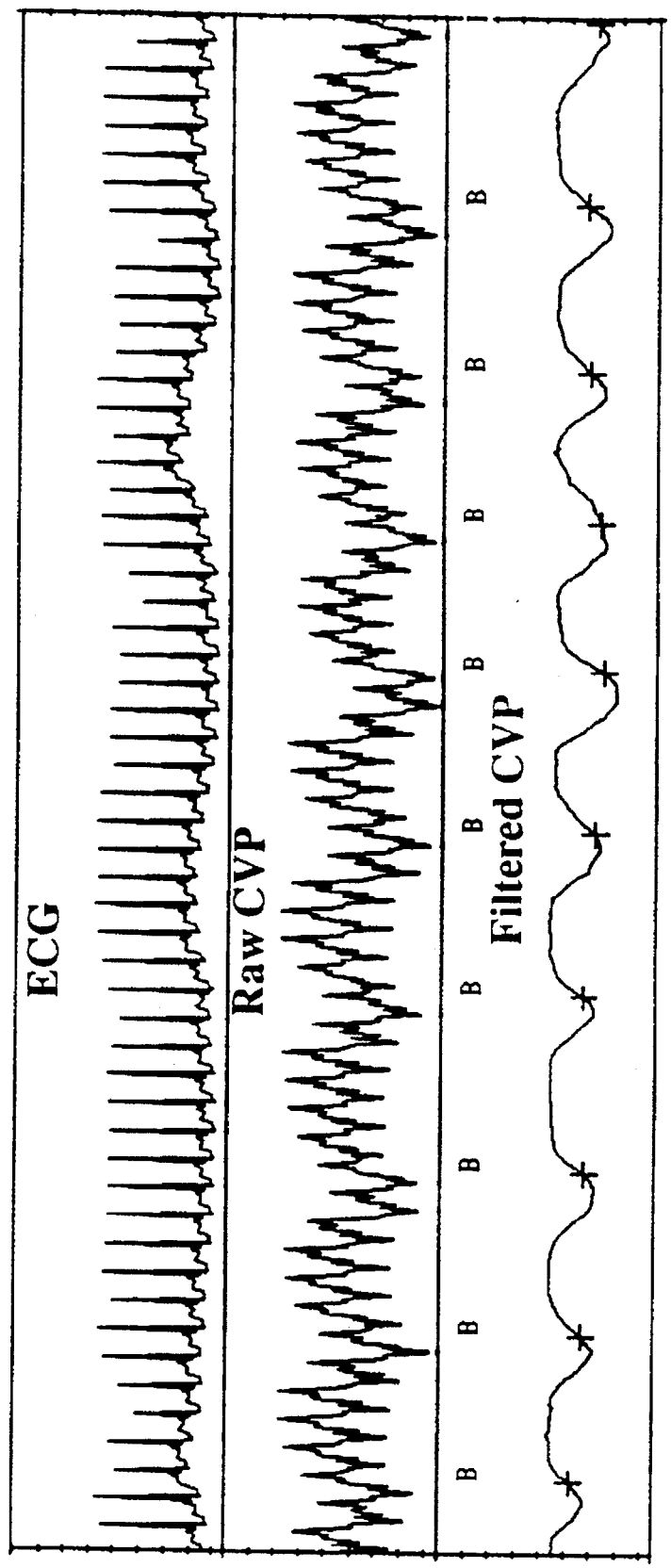
FIG. 7 shows the different stages of filtering the patient signal using the invention.

FIG. 7 shows the different stages of filtering the composite signal. The ECG signal is taken as the reference cardiac signal 10 and the central venous pressure (CVP) signal is used as the composite signal 12, which contains cardiac artifacts. The filtered CVP signal, a time average of the sampled composite signal minus the cardiac frequency and associated harmonics, can be used for subsequent analysis by a computer or by trained medical personnel: trained medical personnel are much better at pattern recognition, i.e. visually curve fitting the original signal, while a computer can monitor patients simultaneously without fatigue. Thus, a time-averaging method allows the computer to assist with monitoring the patients. The composite signal is modulated by notching out the cardiac frequency and any associated harmonic frequencies. The filtered composite signal can be further analyzed to show signal features such as peaks and valleys.

Figure 8A:
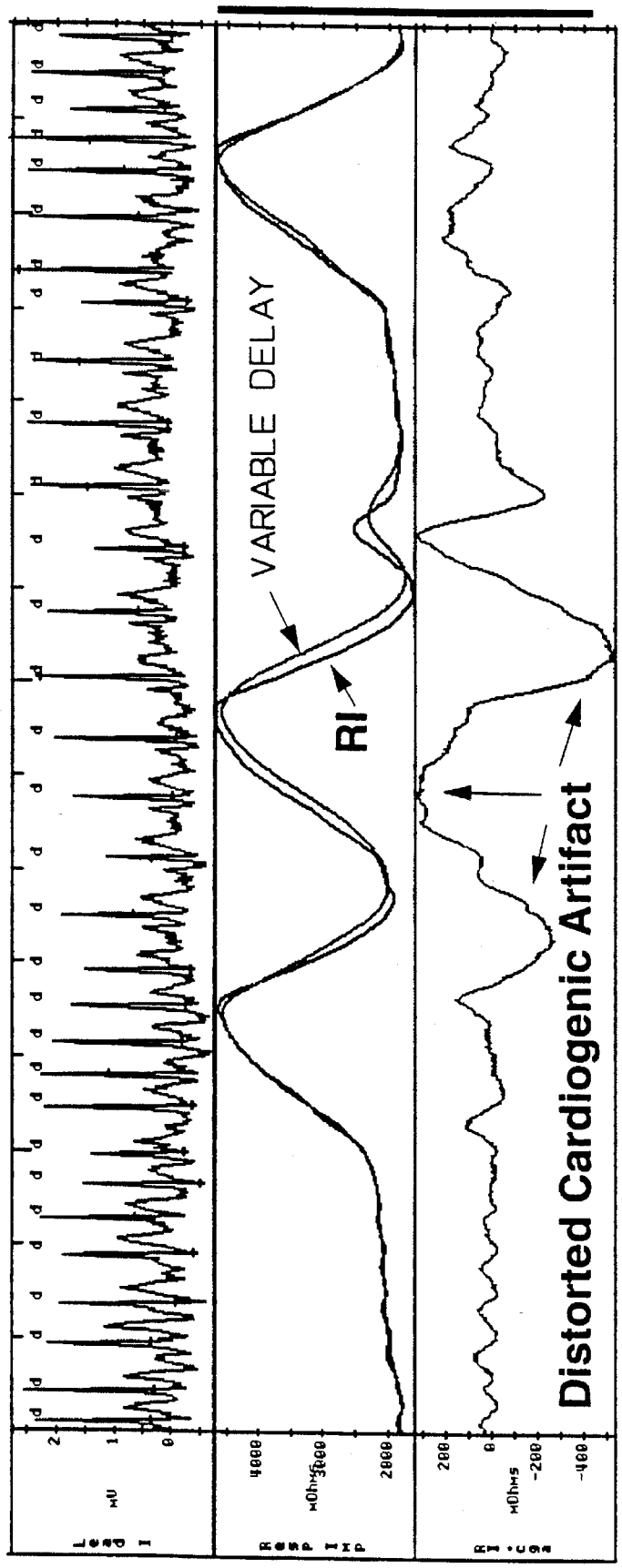
FIG. 8 shows the results of subsequent processing of the composite signal to provide additional cardiac information.
Figure 8B:
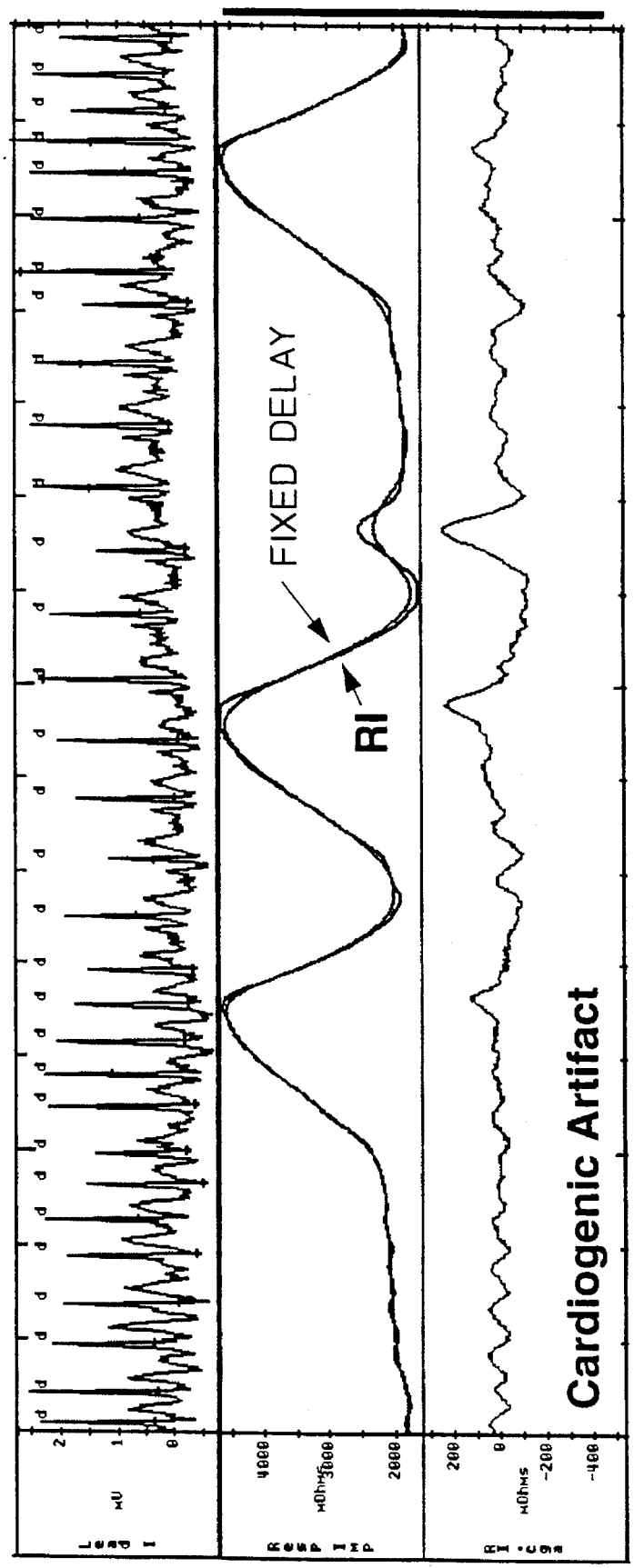

FIG. 8A and 8B illustrate filtering a respiratory signal (RI) to determine the cardiac artifacts. The ECG signal is taken as the reference cardiac signal and the respiratory signal (RI) is used as the composite signal 12 which contains cardiac artifacts. In FIG. 8A. the cardiac artifact is removed from the respiratory signal (RI) using a dynamic filter having a variable delay. In FIG. 8B, the cardiac artifact is removed from the respiratory signal (RI) using a dynamic filter having a fixed delay, according to the invention. Less distortion is introduced into the filtered respiratory signal when a FIR filter having a fixed delay is used.

We claim:

1. A patient monitor, receiving a cyclical cardiac signal and a composite signal containing cardiac artifacts from a patient, comprising:

a sampler, detecting the composite signal at a fixed rate, generating composite samples from the composite signal;

a cardiac event detector, detecting the cyclical cardiac signal, and generating a marked stable reference point for each cardiac cycle;

a cardiac interval detector, detecting the marked stable reference points and generating a cardiac output signal having a variable cardiac frequency and associated harmonics, wherein the variable cardiac frequency corresponds to a cardiac interval between adjacent marked stable reference points;

memory, detecting and storing the composite samples, having a left and a right composite sample pointer;

a first digital filter having a fixed delay, connected to the memory, having an adaptive window with a midpoint and two edges defining a length, wherein one edge corresponds to the left composite sample pointer and the other edge corresponds to the right composite sample pointer, wherein the midpoint corresponds to the composite sample centered between two adjacent reference points, for removing events which occur at the variable cardiac frequency and the associated harmonics and producing a filtered composite signal; and memory controlling means, connected to the memory and detecting the cardiac output signal, for updating the left and right sample pointers such that the length of the adaptive window is equal to the cardiac interval when the midpoint is between two of the marked stable reference points;

wherein the filtered composite signal is produced by removing events which occur at the variable cardiac frequency and the associated harmonies of the cardiac frequency from the composite signal such that the cardiac artifacts are reduced.

2. A patient monitor as defined in claim 1, wherein the first digital filter is a finite impulse response filter.

3. A patient monitor, as defined in claim 2, further comprising:

a feature extractor, detecting the filtered composite signal, generating a first output signal having a frequency which corresponds to signal features of the filtered composite signal, and a second output signal which corresponds to durations between the signal features; and a rate detector, detecting the second output signal and generating a rate output signal corresponding to the first output signal.

4. A patient monitor as defined in claim 3, further comprising:

a patient condition indicator;

evaluation means, connected to the patient condition indicator and the rate detector, for evaluating the rate output signal with at least one patient threshold and activating the patient condition indicator.

5. A patient monitor as defined in claim 4, further comprising a second finite impulse response filter detecting the filtered composite signal and the composite signal, generating an output signal by subtracting the filtered composite signal from the composite signal.

6. A patient monitor as defined in claim 2, wherein the first finite impulse response filter has zeros which correspond to the variable cardiac frequency and its harmonics.

7. A patient monitor as defined in claim 6, wherein the patient monitor is adapted such that the length of the adaptive window is the cardiac interval.

8. A patient monitor as defined in claim 7, wherein the first finite impulse response filter is a rectangular filter.

9. A patient monitor as defined in claim 8, wherein the sampler is adapted to detect a respiratory signal as the composite signal.

10. A patient monitor as defined in claim 8, wherein the sampler is adapted to detect a blood pressure signal as the composite signal.

11. A patient monitor as defined in claim 1, further comprising a second finite impulse response filter detecting the filtered composite signal and the composite signal, generating an output signal by subtracting the filtered composite signal from the composite signal.

12. A patient monitor as defined in claim 1, wherein the cardiac event detector is adapted to detect an electrocardiogram signal.

13. A patient monitor as defined in claim 1, wherein the cardiac event detector is adapted to detect a blood pressure signal.

14. A filtering method for reducing cardiac artifacts in a composite signal by receiving from a patient a first, second, and third cardiac event and a composite signal containing cardiac artifacts, the filtering method comprising the steps of:

measuring a first and a second cardiac period, wherein the first cardiac period is a duration between the first and second cardiac events, wherein the second cardiac period is a duration between the second and third cardiac events;

sampling the composite signal at a sampling rate so as to produce discrete composite values;

defining a first left and a first right window length such that a summation of the first left and first right window lengths is equal to the first cardiac period;

defining a second left and a second right window length such that a summation of the second left and second right window lengths is equal to the second cardiac period;

storing the discrete composite values in a series of memory addresses;

defining a left and a right window correction factor;

pointing a midpointer to the address containing the discrete composite value corresponding to the midpoint of the first cardiac period;

pointing a left end pointer to an address in the memory addresses containing the discrete composite value corresponding to the first left window length behind the midpointer and a right end pointer to the address containing the discrete composite value corresponding to the first right window length ahead of the midpointer; and producing a filtered composite signal using a finite impulse response filter having a dynamic window length, the step of producing comprising:

averaging the discrete composite values between the left and right end pointers, inclusively;

shifting the midpointer to the next discrete composite value such that there is a fixed delay;

updating the left end pointer such that the left window length is changed at multiples of the left window correction factor when the multiples correspond to an integral number of discrete composite values and the right end pointer such that the right window length is changed at multiples of the right window correction factor when the multiples correspond to an integral number of discrete composite values; and repeating, the steps of averaging, and updating until the midpointer points at the address containing the discrete composite value corresponding to the midpoint of the next cardiac interval.

15. A filtering method as defined in claim 14, further comprising the steps of:

detecting signal features of the filtered composite signal; and determining a rate at which the signal features occur.

16. A filtering method as defined in claim 15, further comprising the steps of:

comparing the rate with at least one patient tolerance region; and activating an alarm when the rate is not within the patient tolerance region.

17. A filtering method as defined in claim 16, further comprising the step of subtracting the filtered composite signal from the composite signal such that the filtered composite signal is substantially removed from the composite signal.

18. A filtering method as defined in claim 15, wherein the step of sampling the composite signal samples a respiratory signal.

19. A filtering method as defined in claim 15, wherein the step of sampling the composite signal samples a blood pressure signal.

* * * * *